United States Patent [19]

Schaeffer

[11] Patent Number: 5,577,516
[45] Date of Patent: Nov. 26, 1996

[54] INTRAVENOUS CATHETER SUPPORT

[75] Inventor: Rodney D. Schaeffer, Bellefonte, Pa.

[73] Assignee: Stat Emergency Medical Products, Inc., Bellefonte, Pa.

[21] Appl. No.: 217,336

[22] Filed: Mar. 24, 1994

[51] Int. Cl.[6] ..................................... A61F 5/37
[52] U.S. Cl. ..................... 128/877; 602/42; 128/888
[58] Field of Search ...................... 128/846, 869, 128/877–879, 888, DIG. 26; 602/41, 42

[56] References Cited

U.S. PATENT DOCUMENTS

| | | | |
|---|---|---|---|
| 3,194,235 | 7/1965 | Cooke | 128/DIG. 26 |
| 3,196,870 | 7/1965 | Sprecher et al. | 128/133 |
| 3,376,865 | 4/1968 | Gamper | 128/169 |
| 3,423,095 | 1/1969 | Cox | 273/189 |
| 3,633,567 | 1/1972 | Sarnoff | 128/2.05 C |
| 3,640,273 | 2/1972 | Ray | 128/87 |
| 3,719,187 | 3/1973 | Ulansey | 128/90 |
| 3,722,508 | 3/1973 | Roberts | 128/877 |
| 3,745,998 | 7/1973 | Rose | 128/89 R |
| 3,814,080 | 6/1974 | Norman | 128/DIG. 26 |
| 3,815,588 | 6/1974 | Klausner | 128/77 |
| 3,827,107 | 8/1974 | Moore | 24/16 R |
| 4,048,991 | 9/1977 | Marx | 128/165 |
| 4,149,540 | 4/1979 | Hasslinger | 128/327 |
| 4,151,842 | 5/1979 | Miller | 128/87 R |
| 4,198,989 | 4/1980 | Hawke et al. | 128/877 X |
| 4,224,937 | 9/1980 | Gordon | 128/DIG. 26 |
| 4,273,130 | 6/1981 | Simpson | 128/327 |
| 4,436,088 | 3/1984 | Finnieston | 128/77 |
| 4,453,933 | 6/1984 | Speaker | 128/877 X |
| 4,502,477 | 3/1985 | Lewis | 128/133 |
| 4,606,735 | 8/1986 | Wilder et al. | 128/DIG. 26 |
| 4,633,863 | 1/1987 | Filips et al. | 128/877 X |
| 4,671,787 | 6/1987 | Widman | 604/179 |
| 4,870,976 | 10/1989 | Denny | 128/888 X |
| 4,898,587 | 2/1990 | Mera | 128/DIG. 26 |
| 4,919,150 | 4/1990 | Grunt | 128/877 |
| 4,928,712 | 5/1990 | Mele | 128/877 |
| 5,084,026 | 1/1992 | Shapiro | 128/DIG. 26 |
| 5,238,010 | 8/1993 | Grubenkort et al. | 128/888 |
| 5,266,401 | 11/1993 | Tollini | 128/877 X |
| 5,413,120 | 5/1995 | Grant | 128/877 |

FOREIGN PATENT DOCUMENTS 1003251  11/1951  France ..................... 128/DIG.26

Primary Examiner—Robert A. Hafer
Assistant Examiner—Brian E. Hanlon
Attorney, Agent, or Firm—Panitch Schwarze Jacobs & Nadel, P.C.

[57] ABSTRACT

A plurality of devices are provided for dressing wounds, injuries, and inserted intravenous (IV) catheters on a body portion of a patient. Each device has a pressure plate for being positioned in engagement with the wound, injury, or inserted IV catheter, and at least one securing strap to secure the pressure plate in engagement therewith. An embodiment having a bandage secured to an elongated pressure plate with a flexible center portion may be applied to a wound in the area of a body joint. Another embodiment having a bandage secured to each of two pressure plates may be applied to a wound comprising first and second wound areas located in the same general lateral portion of a body portion. Still another embodiment having a raised portion at one end of the pressure plate generally shaped to correspond to the external portion of an inserted IV catheter may be applied to secure the IV catheter. In the embodiments, the strap and the bandage may be adhesively or sonically secured to the pressure plate and the edges of the pressure plate may be blunted to provide the patient comfortable contact therewith. The portion of the strap extending from the pressure plate may be initially pre-rolled and detachably anchored out of the way of the wound contacting surface such that a device can be quickly positioned and the strap can be quickly unrolled, passed around the body portion, and secured to the pressure plate.

6 Claims, 3 Drawing Sheets

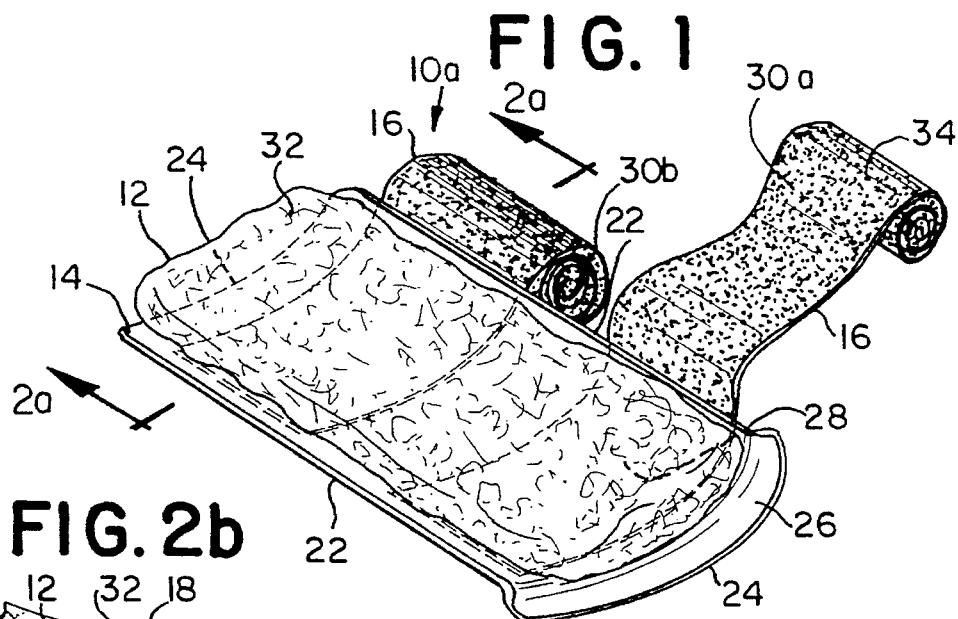
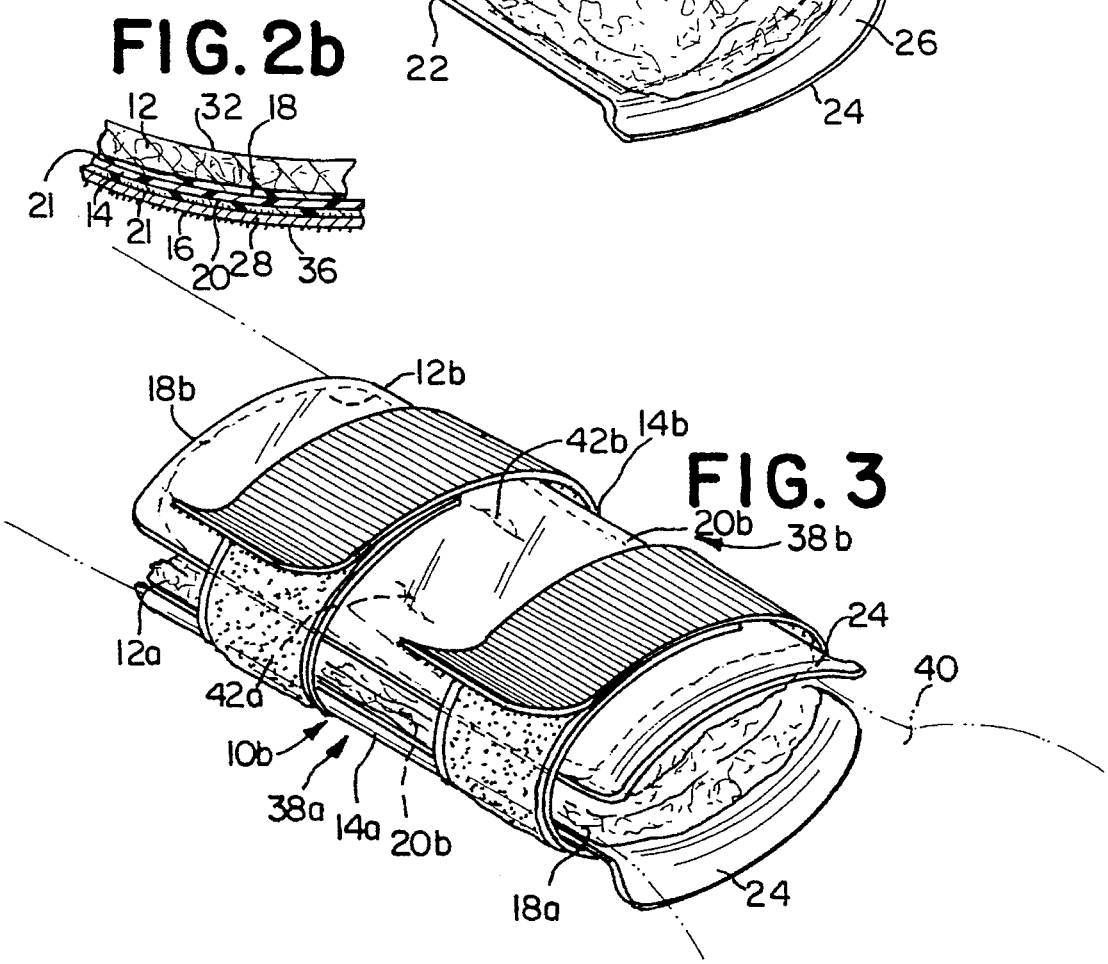

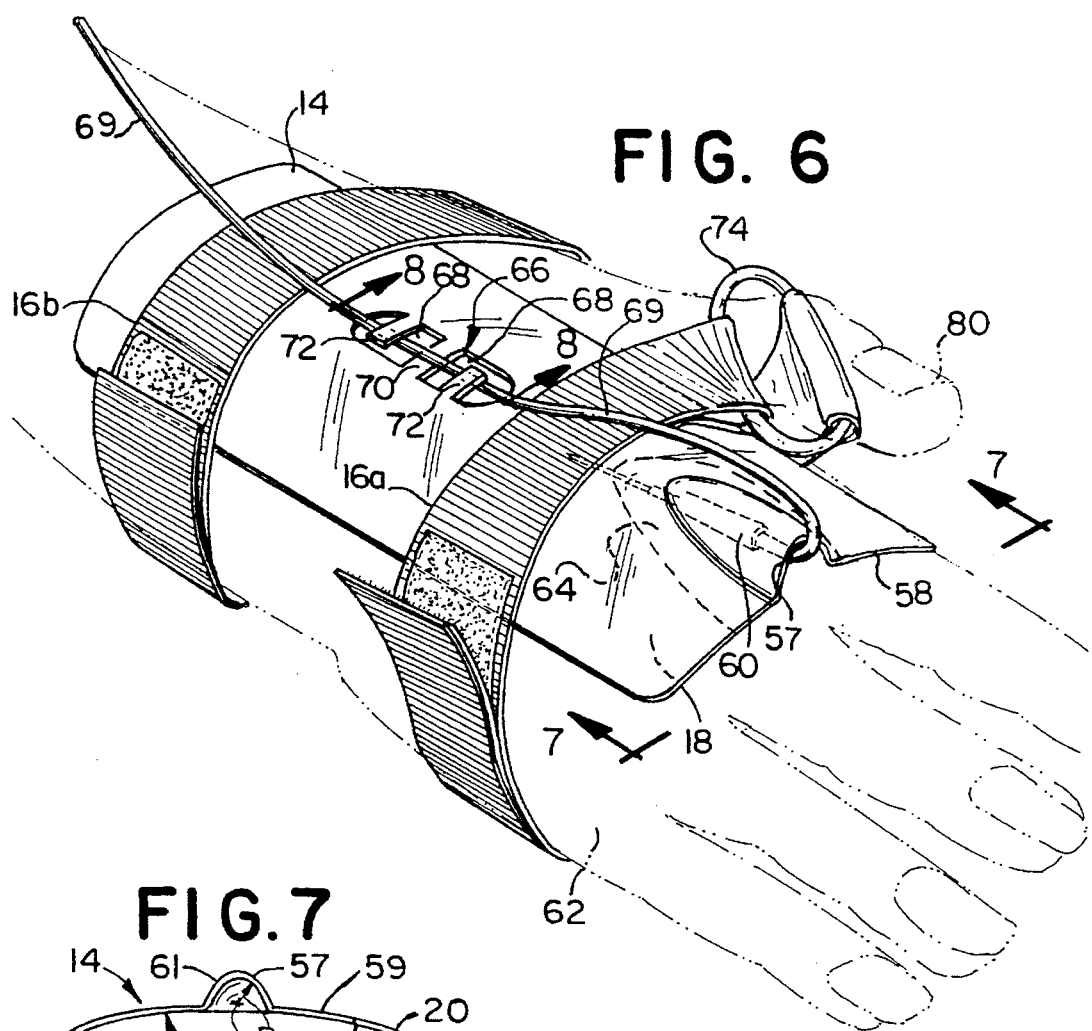

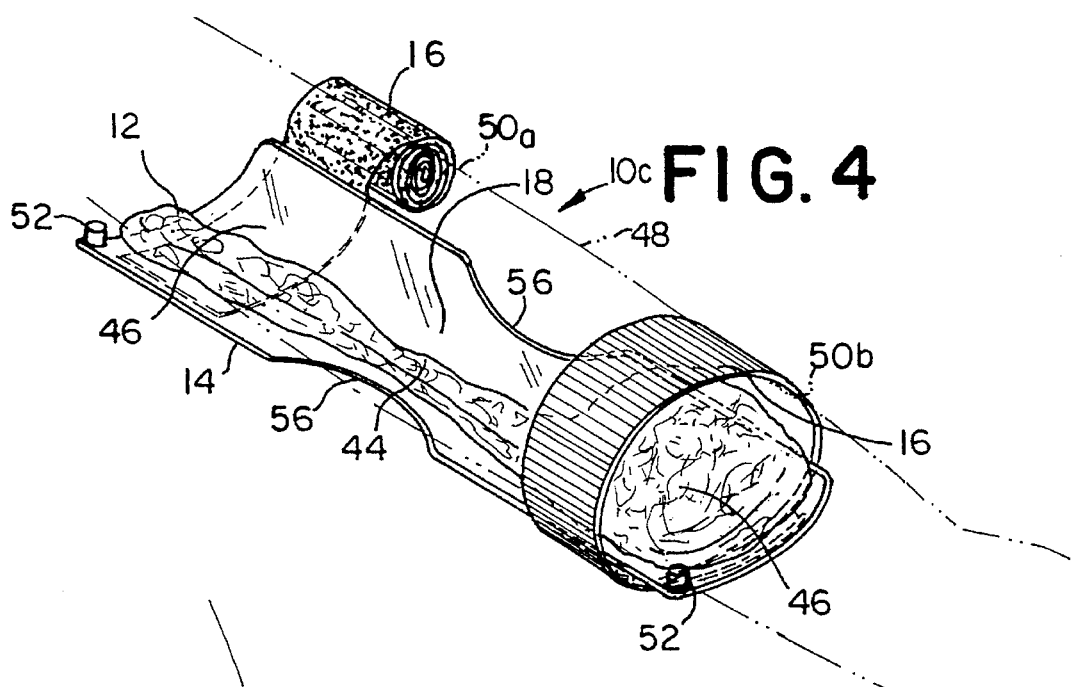
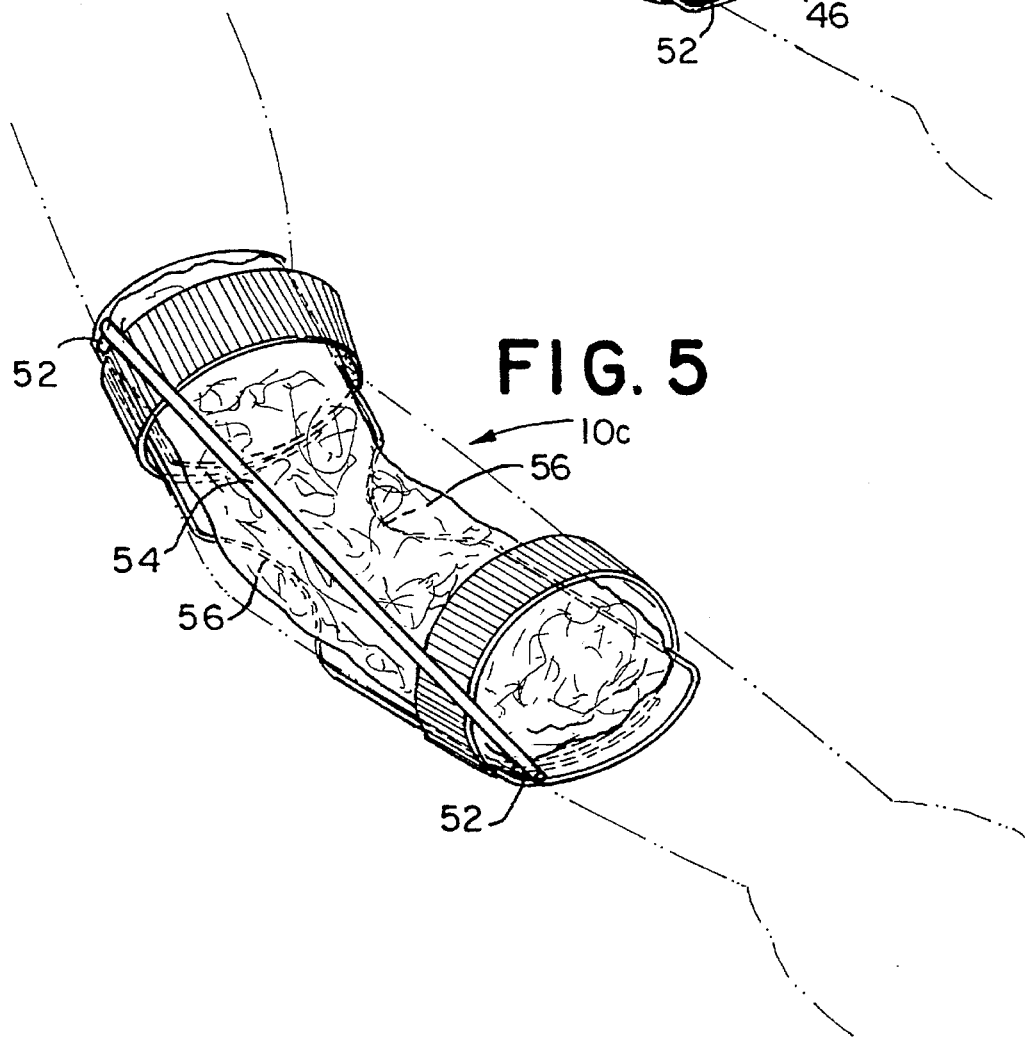

INTRAVENOUS CATHETER SUPPORT

BACKGROUND OF THE INVENTION

The present invention relates generally to devices for dressing wounds, injuries, and/or inserted intravenous (IV) catheters under sterile and/or field emergency conditions. More particularly, the invention relates to devices that can be quickly positioned on and secured to a body portion to protect and/or apply pressure to the wounds, injuries, or inserted IV catheters.

Presently, medical personnel generally utilize tape, cloth, plastic, or flexible adhesive means to fasten bandages and the like over wounds, injuries, and/or inserted IV catheters on patients. Such adhesive means require that strips of paper, cloth, or plastic adhesive tape or similar material (hereinafter generally referred to as "tape") be individually cut and trimmed to fasten the bandage or IV catheter directly to the skin of a patient. As may be recognized, such means are time-consuming in that a medical worker attending to the patient is required, for example, to unroll the tape, measure out appropriate lengths, cut the tape at the appropriate length, and affix the cut tape to the patient in a proper manner. If the bandage is particularly large or if several bandages are required, as may be the case in an emergency trauma situation involving multiple wounds, the time consumed may be life threatening.

Moreover, the traditional means of fastening a bandage to a wound, as outlined above, may require even more time, especially in situations where the bandage must be frequently changed, or if fluids or the condition of the skin of a patient prevent proper adhesion of the adhesive tape. Similarly, when a bandage is removed to check a wound, the adhesive material traditionally used tends to lose the ability to stick, resulting in a need for an entirely new bandage or at least new tape.

With respect to inserted IV catheters, medical personnel generally affix one or more lengths of adhesive tape to hold the catheter in place and prevent foreign contaminants from contacting the entry point on the skin of the patient. However, and again, the tape may have to be re-applied should fluids or the condition of the skin of the patient prevent proper adhesion. Moreover, the removal of the tape may actually tear the skin from the patient, especially if the patient is older.

In situations such as mass disasters or military field conditions, or when faced with treating single patients with life threatening injuries under extreme time constraints, medical personnel have found the piecemeal traditional methods of dressing the injuries, wounds, and inserted IV catheters to be unacceptable.

SUMMARY OF THE INVENTION

The present invention is directed to devices for dressing wounds, injuries, and inserted IV catheters on a body portion of a patient.

In a first preferred embodiment, the device comprises a bandage secured to an inner surface of a pressure plate for being positioned in engagement with a wound on a body portion and at least one securing strap attached to the pressure plate. The strap may be passed around the body portion and secures the pressure plate with the bandage in engagement with the wound. Preferably, the strap and the bandage are adhesively or sonically secured to the outer and inner surfaces, respectively, of the pressure plate and at least one of the edges of the pressure plate is blunted to provide the patient comfortable contact therewith.

Preferably, the strap has a fixed portion secured to the pressure plate and a free portion extending from the fixed portion. Preferably, the free portion is initially pre-rolled and detachably anchored to the outer surface of the pressure plate out of the way of the wound contacting surface of the bandage. Thus, the bandage may be quickly positioned in engagement with the wound and the free portion of the strap may be quickly unrolled, passed around the body portion, and secured to the pressure plate.

In a second preferred embodiment, the device has first and second members attached to one another by a strap, and each member has a bandage secured to the inner surface of a pressure plate. Thus, each member may be positioned in engagement with a separate wound area on the body portion of the patient where the separate wound areas are at approximately the same lateral portion of the body portion, and the strap can be passed around the body portion to secure the members in engagement with the separate wound areas.

In a third preferred embodiment, the pressure plate of the first embodiment is elongated and has a flexible center portion and elongated end portions extending in opposite directions from the flexible center portion. Thus, the pressure plate may be positioned in engagement with a wound in the area of a body joint connecting first and second body members. Accordingly, the elongated portions engage the first and second body members and the flexible center portion is positioned in the area of the joint. At least one securing strap is attached to each elongated end portion and is passed around a respective body member to secure the pressure plate with the bandage in engagement with the wound while allowing the joint to be rested in a plurality of positions. Preferably, a fixing member may be attached to securing devices on each elongated end portion to fix the joint in a predetermined position.

In a fourth preferred embodiment, the device secures an intravenous (IV) catheter inserted into a body portion of a patient and comprises a pressure plate with a raised portion at one end generally shaped to correspond to the external portion of the inserted IV catheter. The pressure plate is positioned in engagement with the body portion and the IV catheter when the IV catheter is installed in the body portion to secure the IV catheter to the body portion. At least one securing strap is passed around the body portion to secure the pressure plate and the IV catheter to the body portion.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings:

FIG. 1 shows a perspective view of a first embodiment of the present invention comprising a device having a pressure plate with a dressing and a securing strap attached thereto;

FIG. 2a is a cross-sectional view of the device shown in FIG. 1 taken along the line 2a —2a;

FIG. 2b is an enlarged scale view of a portion of FIG. 2a;

FIG. 3 is a perspective view of a second embodiment of the present invention showing a device comprising first and second pressure plates and dressings and at least one securing strap attached to both plates;

FIG. 4 is a perspective view of a third embodiment of the present invention showing a device having an elongated pressure plate with a flexible center portion;

FIG. 5 is a perspective view of the device of FIG. 4 showing a flexed pressure plate and a fixing member fixing the angle of the flex;

FIG. 6 is a perspective view of a fourth embodiment of the present invention showing a device comprising a pressure plate having an IV catheter securing portion, and at least one securing strap; and FIGS. 7 and 8 are cross-sectional views of the device of FIG. 6 taken along the lines 7—7 and 8—8, respectively.

DETAILED DESCRIPTION OF PREFERRED EMBODIMENTS

Certain terminology may be used in the following description for convenience only and is not limiting. The words "left", "right", "upper", and "lower" designate directions in the drawings to which reference is made. The words "inwardly" and "outwardly" are further directions toward and away from, respectively, the geometric center of a referenced element. The terminology includes the words above specifically mentioned, derivatives thereof, and words of similar import.

Referring to the drawings in detail, wherein like numerals are used to indicate like elements throughout, there is shown in FIG. 1 a first embodiment of a trauma dressing device 10a for dressing a wound or injury on a body portion of a patient. As seen, the device 10a includes a bandage 12, a pressure plate 14, and at least one but preferably two or more securing straps 16. The pressure plate 14 has an inner surface or side 18 and an outer surface or side 20, the bandage 12 is preferably secured to the inner surface 18, and the securing strap 16 is preferably secured to the outer surface 20.

The pressure plate 14 with the bandage 12 is designed to be positioned in engagement with a wound (not shown in FIG. 1) such that the bandage 12 firmly contacts the wound. When positioned as such, the securing straps 16 are passed around the body portion (not shown in FIG. 1) to secure the pressure plate 14 with the bandage 12 in firm engagement with the wound.

As may be recognized, the bandage 12 may comprise any kind of bandage including a cloth bandage, a cotton bandage, a polymeric bandage, and the like. Moreover, the bandage 12 may be particularly suited for one or more functions including applying pressure to a wound, absorbing a particular bodily fluid, protecting a wound or injury from external contaminants, and the like.

Preferably, the pressure plate 14 comprises a generally longitudinally extending sheet of material and, as seen in FIG. 2a, is generally curved in transverse cross-section. Preferably, the material is a generally rigid material capable of having pressure applied thereto and also capable of applying pressure to the area of the body portion proximate the wound in a generally uniform manner. The generally rigid material may comprise polycarbonate, rubber, dense foam, acrylic, polystyrene, plastic, synthetic resin, composite material, sheet aluminum, sheet metal, or combinations thereof. As will be recognized, however, the pressure plate 14 may also comprise any other suitable materials. More preferably, the pressure plate 14 comprises approximately 4 mil thick polycarbonate, and the pressure plate is transparent to permit observation therethrough.

Preferably, pressure plate 14 has a pair of longitudinally oriented sides 22 and a pair of laterally oriented sides 24, where each side 22 and 24 has an edge and at least one of the edges 22 or 24 is blunted or curled 26. As seen in FIGS. 1 and 2a, respectively, the blunted edge 26 on the longitudinal side 22 and the curled edge 26 on the lateral side 24 allow a patient to comfortably contact the generally rigid longitudinal and lateral sides 22, 24 without experiencing undue sharpness therefrom.

Preferably, the device 10a has as many securing straps 16 as may be necessary, depending upon the longitudinal length of the bandage 12 and pressure plate 14, to secure the pressure plate 14 and apply adequate pressure to all longitudinal portions of the bandage 12 and the wound. Preferably, the securing straps 16 may be used to secure the bandage 12 and the pressure plate 14 to the wound with such pressure as may be necessary to, for example, staunch the flow of blood. Also preferably, the securing straps 16 are adjustable such that the pressure may be increased or decreased, as desired.

Preferably, the straps 16 comprise a sturdy material such as woven nylon thread that will not break when applying pressure to the wound. Also preferably, the straps are at least as long as may be necessary to completely pass around the body portion, and wide enough such that the strap does not dig in to exposed skin on the body portion or otherwise provide undue irritation. For example, the straps 16 may be approximately one inch wide and eighteen inches long to pass around an average-size upper leg. As will be recognized, however, the straps may comprise any other appropriate material and be any other appropriate length and width.

As seen in FIG. 2b, the bandage 12 and the straps 16 may be secured to the inner and outer surfaces 18, 20, respectively, of the pressure plate 14 via any of several well-known adhesives 21. Alternatively, the bandages 12 and the straps 16 may be secured to the pressure plate 14 by sonic welding. As may be recognized, sonic welding entails fusing the outer surface 20 of pressure plate 14 directly to the straps 16, and the inner surface 18 of the pressure plate 14 directly to the bandage 12. Other methods may alternatively be used to secure the straps 16 and/or the bandage 12 to the pressure plate 14 if desired.

Preferably, and as seen in FIG. 1, each strap 16 has a fixed portion 28 which is secured directly to the pressure plate 14 and a free portion 30a or 30b extending from the fixed portion 28. Preferably, the free portions 30a and 30b are initially pre-rolled and detachably anchored to the outer surface 20 of the pressure plate 14. Free portion 30b is shown in such an initial condition. Preferably, the detachable anchoring is accomplished by at least a portion of the surface of each of the straps 16 and at least an area on the outer surface 20 of the pressure plate 14 comprising a hook and loop fastening system, as will be described below. However, it will be recognized that other anchoring means may be employed.

Being rolled and anchored as such, the straps 16 are positioned out of way of the wound contacting surface 32 of the bandage 12, and the bandage 12 may be quickly positioned in engagement with the wound without any hinderance from the straps 16. Moreover, the pre-rolled free portion 30b may then be quickly unrolled by hand or under the influence of gravity after being released, passed around the body portion, and secured to the pressure plate 14. In order to pre-roll the straps 16, a small cardboard tube (not shown) or the like may be employed as the core of the roll.

Preferably, the device 10a has a hook fastening portion 34 (as seen in FIG. 1) and a loop fastening portion 36 (as seen in FIGS. 2a and 2b). Preferably, one of the hook fastening portion 34 and the loop fastening portion 36 is secured to the free portion 30 of the straps 16 and the other of the hook fastening portion 34 and the loop fastening portion 36 is secured proximate the fixed portion 28 of the straps 16. As seen in FIGS. 1, 2a and 2b, the hook fastening portion 34 is attached to the free portion 30 of the straps 16 and the loop fastening portion 36 is attached directly to the fixed portion 28 of the straps 16. However, it will be recognized that the portion 34, 36 secured proximate the fixed portion 28 of the straps 16 need not necessarily be secured directly to the fixed portion 28. With the hook and loop portions 34, 36 secured as such, the straps 16 secure the pressure plate 14 with the bandage 12 in place when the straps 16 are passed around the body portion and when the hook fastening portion and the loop fastening portion 34, 36 engage one another.

Referring now to FIG. 3, there is shown another trauma dressing device 10b in accordance with a second preferred embodiment of the invention. The device 10b is preferably for use in trauma situations where there are separate wound areas 42a, 42b on the same general lateral portion of a generally longitudinal body portion 40 of a patient, and accordingly comprises first and second members 38a, 38b. As with the first embodiment of the present invention, each member 38a, 38b has a bandage 12a, 12b and a pressure plate 14a, 14b, and the bandages 12a, 12b are secured to the inner surfaces 18a, 18b of the pressure plates 14a, 14b, respectively. Thus, each member 38a, 38b is respectively positioned in engagement with a separate wound area 42a, 42b on the body portion 40.

As with the first embodiment, the second embodiment also has at least one and preferably two or more securing straps 16. However, the straps 16 in the second embodiment are attached to the outer surface 20a of pressure plate 14a of the first member 38a and the outer surface 20b of pressure plate 14b of the second member 38b. Thus, with the first and second members 38a, 38b positioned in engagement with the wound areas 42a, 42b, the straps 16 pass around the body portion 40 and are secured to hold the members 38a, 38b and the bandages 12a, 12b in place.

Preferably, the body portion 40 is an upper or lower arm or leg, the wound areas 42a, 42b are in approximately the same lateral area of the limb, and the members 38a, 38b are sized and shaped to surround and conform generally to the limb. As will be recognized, the wound areas 42a, 42b need not necessarily be distinct, but may in fact comprise a single extensive wound or injury.

As can be seen in FIG. 3, the pressure plates 14a, 14b each have a longitudinal axis generally parallel with respect to one another, and each strap 16 is generally transversely attached to each of the pressure plates 14a, 14b. Each strap 16 is fixed to both pressure plates 14a, 14b, and as with the first embodiment, a free portion 30 extends from one of the fixed portions 28a, 28b. Preferably, each strap 16 includes a sufficient span between the fixed portions 28a, 28b such that, when the device 10b is mounted to a body portion 40, each pressure plate 14a, 14b may fully contact the respective wound areas 42a, 42b. One of the fixed portions 28a or 28b may be detachably secured by way of a hook-and-loop fastening arrangement or the like in order to facilitate the positioning of the members 38a, 38b.

Referring now to FIG. 4, there is shown another trauma dressing device 10c in accordance with a third preferred embodiment of the present invention. As with the first embodiment, the third embodiment includes a bandage 12 (shown partially cut away in FIG. 4), a pressure plate 14, and at least one but preferably two or more straps 16, and the bandage 12 is secured to the inner surface 18 of the pressure plate 14. However, the pressure plate 14 of the third embodiment has a flexible center portion 44 and first and second elongated end portions 46 extending in opposite directions from the flexible center portion 44. Thus, the pressure plate 14 with the bandage 12 may be positioned in engagement with a single wound or multiple wounds (shown in FIG. 5) in the area of a body joint 48 connecting first and second body members 50a, 50b. As positioned, the first and second elongated portions 46 and the flexible center portion 44 engage the first and second body members 50a, 50b and the area of the body joint 48, respectively.

The trauma dressing device 10c of the third embodiment has at least one securing strap 16 attached to each elongated end portion 46a, 46b. In order to secure the pressure plate 14 with the bandage 12 in engagement with the wound(s), each strap 16 is passed around the respective body member 50a, 50b and is secured in the manner described above. The flexible center portion 44 permits the pressure plate 14 to be flexed to allow the body joint 48 to be moved and/or rested in a plurality of positions.

Preferably, the device 10c is positioned in engagement with one or more wounds in the area of an elbow or a knee. Also preferably, the device 10c may be flexed and fitted to the inside or the outside of the elbow, knee or other joint.

Preferably, and as seen in FIG. 5, each elongated end portion 46 has a securing member 52 and the device 10c also includes an elongated fixing member 54. The securing members 52 are designed to receive and secure a portion of the elongated fixing member 54 to the respective end portion 46. With the elongated fixing member 54 secured to each elongated end portion 46 of the pressure plate 14 by way of the securing members 52, the device 10c and the body joint 48 are fixed in a predetermined flexing position.

As may be recognized, a second elongated fixing member 54 and corresponding securing members (not shown) may be provided on the opposite side of the device 10c. Additionally, the elongated fixing member 54 may be any elongated member suitable for the purpose of fixing the body joint 48 at a predetermined flexing position. Such an elongated fixing member 54 may include a plastic or metal rod, a wood dowel, or the like, and each securing member 52 may comprise any suitable mechanism for securely clamping onto the elongated fixing member 54. For example, prongs (not shown) may extend outwardly from the pressure plate 14, the elongated fixing member 54 being snapped in between the prongs.

In order to provide the flexibility required at the flexible center portion 44, it is preferable that the pressure plate 14 of the device 10c have a pair of notches 56 extending inwardly from either longitudinal side. As will be appreciated, such notches 56 allow the pressure plate to be a single piece of material that integrally incorporates the flexible center portion 44 and the elongated end portions 46. Preferably, each notch 56 has a generally semi-circular shape.

Referring now to FIG. 6, there is shown another trauma dressing device 10d in accordance with a fourth preferred embodiment of the present invention. As with the first embodiment, the device 10d of the fourth embodiment has a pressure plate 14 and at least one but preferably two or more straps 16 (seen as 16a or 16b in FIG. 6). However, since the device 10d is for dressing an inserted intravenous (IV) catheter 60, a bandage is not required. Instead, and as seen in FIGS. 6 and 7, the pressure plate 14 has a raised portion 57 proximate one longitudinal end. More particularly, and referring to FIG. 7, the pressure plate 14 has in transverse cross-section a first, major curvature 59 defined by a first general radius $R_1$ extending from a center point $C_1$. As seen, the first curvature 59 defines the inner side 18 and outer side 20 of the pressure plate 14, and the raised portion 57 extends outwardly from the outer side 20 of the pressure plate 14 and has in transverse cross-section a second, minor curvature 61 defined by a second general radius $R_2$ extending from a center point $C_2$, smaller than the first general radius $R_1$. As should be understood, the first and second curvatures 59, 61 need not necessarily be true radial arcs and, therefore, first and second general radius $R_1$, $R_2$ need not be exact radii. Preferably, the one end of the pressure plate 14 has an edge 58 and the raised portion 57 extends a distance away from the edge 58 toward the opposite end of the pressure plate 14.

As can be seen in FIG. 6, the raised portion 57 is generally shaped to correspond to the external portion of the IV catheter 60 when the catheter 60 is inserted into a body portion 62 of a patient. Thus, the pressure plate 14 of the device 10d is sized and shaped to be positioned in engagement with the body portion 62 and the IV catheter 60. Once the pressure plate 14 is positioned, the straps 16 are passed around the body portion 62 to secure the pressure plate 14 and the IV catheter 60.

Although not essential, the inner surface 18 of the pressure plate 14 proximate the raised portion 57 may have a small quantity of an adhesive material 64 placed thereon for holding the pressure plate 14 and the IV catheter 60 in place on the body portion 62. Preferably, the adhesive material 64 is a two-sided adhesive tape. As will be recognized, any two-sided adhesive tape generally used for medical purposes may be employed. The device 10d may also have a bandage (not shown), although such a bandage is not essential, either.

Preferably, the pressure plate 14 of the trauma dressing device 10d further comprises an IV line holder 66 for securing a portion of the IV line 66 extending from the IV catheter 60 to the pressure plate 14. Preferably, the IV line holder 66 comprises a pair of adjacent apertures 68 on the pressure plate 14, where the apertures 68 are separated by a bridge 70. Also preferably, first and second tabs 72 respectively extend from the pressure plate 14 into the first and second apertures 68 generally in parallel with each other and with the bridge 70 and in generally opposite directions. The tabs 72 are sufficiently flexible that they may be slightly lifted and a portion of the IV line may be positioned underneath. Thus, and as best seen in FIG. 8, the IV line holder 66 secures a portion of the IV line 69 when the line 69 is positioned to straddle the bridge 70 and when the portion of the line 69 adjacent each tab 72 is positioned under the tab 72 and adjacent the body portion 62.

Preferably, the pressure plate 14 of the device 10d is longitudinally oriented and the first and second tabs 72 and the bridge 70 extend generally transversely with respect to the pressure plate 14. However, it will be recognized that the first and second tabs 72 and the bridge 70 may extend longitudinally. Preferably, the apertures 68, the bridge 70, and the tabs 72 are integrally formed with the pressure plate 14 of the device 10d of the same material, and the bridge 70, and the tabs 72 comprise the same material as the pressure plate 14. More preferably, the bridge 70, the tabs 72, and the pressure plate 14 are formed together from a single mold.

Preferably, the IV catheter 60 is inserted on the back side of a hand of a patient (as seen in FIG. 6) and the device 10d comprises at least two securing straps 16a, 16b attached to the pressure plate 14. The straps 16a, 16b are passed around the hand 16 and a region adjacent the hand. The region may comprise the palm, the wrist or the forearm, depending upon the longitudinal length of the pressure plate 14.

Preferably, one of the straps 16a is a thumb strap. Also preferably, the thumb strap 16a includes a ring 74 interconnecting a fixed strap piece 76 and a free strap piece 78. The ring 74 is positioned on the thumb strap 16a such that the thumb 80 of the hand may be inserted therethrough. With the thumb 80 positioned within the ring, the thumb strap 16a can secure the pressure plate 14 and the IV catheter 60 while at the same time allowing the thumb 80 a degree of mobility without unduly disturbing the secured IV catheter 60. As will be recognized, the ring 74 may also be placed behind or in front of the thumb 80, whichever may be deemed desirable.

From the foregoing description, it can be seen that the present invention comprises new and useful trauma dressing devices. It will be appreciated by those skilled in the art that changes could be made to the embodiments described above without departing from the broad inventive concepts thereof. It is understood, therefore, that this invention is not limited to the particular embodiments disclosed, but is intended to cover modifications within the spirit and scope of the present invention as defined by the appended claims.

In the claims:

1. A device for securing an intravenous (IV) catheter inserted into a body portion of a patient, the IV catheter being attached to an IV line, the device comprising:

a generally longitudinal pressure plate having in transverse cross-section a first, major curvature, the first curvature being defined by a first radius, the first curvature defining an inner side and an outer side of the pressure plate, the pressure plate also having first and second longitudinal ends and a generally longitudinally oriented raised portion beginning at the first end and extending toward the second end, the raised portion extending outwardly from the outer side of the pressure plate and having in transverse cross-section a second, minor curvature, the second curvature being defined by a second radius smaller than the first radius, the pressure plate for being positioned in engagement with the body portion with the raised portion in engagement with the IV catheter to secure the inserted IV catheter to the body portion;

the pressure plate further having first and second adjacent apertures separated by a bridge and first and second tabs extending into the first and second apertures, respectively, the first and second tabs extending generally in parallel with each other and with the bridge and in generally opposing directions, the first and second tabs and the bridge for securing a portion of the IV line to the pressure plate when the portion of the IV line is positioned to straddle the bridge and pass under the tabs adjacent the body portion; and a first securing strap attached to the pressure plate, the first strap for being passed around the body portion for securing the pressure plate and the IV catheter.

2. The device of claim 1 wherein the inner side of the pressure plate is for being positioned adjacent the body portion and wherein the inner side adjacent the raised portion has an adhesive for holding the pressure plate and the IV catheter in place on the body portion.

3. The device of claim 2 wherein the adhesive comprises adhesive tape.

4. The device of claim 1 wherein the pressure plate has a longitudinal axis and the first and second tabs and the bridge extend generally transversely with respect to the longitudinal axis.

5. The device of claim 1 wherein the device further comprises a second securing strap attached to the pressure plate.

6. The device of claim 5 wherein one of the first and second straps is for being passed around a hand of a patient and includes a ring interconnecting a fixed strap piece and a free strap piece, the ring for having a thumb of the hand inserted therethrough when the strap is secured.

* * * * *